(12) United States Patent
Maruhata

(10) Patent No.: US 9,446,570 B2
(45) Date of Patent: Sep. 20, 2016

(54) SHEET ARTICLE MANUFACTURING APPARATUS

(75) Inventor: Kazuya Maruhata, Mima-gun (JP)

(73) Assignee: LIVEDO CORPORATION, Shikokuchuo-shi (JP)

( * ) Notice: Subject to any disclaimer, the term of this patent is extended or adjusted under 35 U.S.C. 154(b) by 248 days.

(21) Appl. No.: 14/127,320

(22) PCT Filed: Jul. 5, 2012

(86) PCT No.: PCT/JP2012/004387
§ 371 (c)(1),
(2), (4) Date: Dec. 18, 2013

(87) PCT Pub. No.: WO2013/008431
PCT Pub. Date: Jan. 17, 2013

(65) Prior Publication Data
US 2014/0138031 A1    May 22, 2014

(30) Foreign Application Priority Data
Jul. 8, 2011    (JP) .................. 2011-151578

(51) Int. Cl.
*B28B 19/00*    (2006.01)
*B29C 65/54*    (2006.01)
(Continued)

(52) U.S. Cl.
CPC ..... *B32B 37/0053* (2013.01); *A61F 13/15658* (2013.01); *A61F 13/15764* (2013.01);
(Continued)

(58) Field of Classification Search
USPC ....... 156/278–280, 390, 547, 548, 553, 555, 156/581, 582
See application file for complete search history.

(56) References Cited

U.S. PATENT DOCUMENTS 3,759,011 A    9/1973    Akke
4,604,852 A    8/1986    Becker
(Continued)

FOREIGN PATENT DOCUMENTS

CN    1988864 A    6/2007
CN    101032436 A    9/2007
(Continued)

OTHER PUBLICATIONS

International Search Report of PCT/JP2012/004387, mailing date of Oct. 9, 2012.
(Continued)

*Primary Examiner* — Sing P Chan
(74) *Attorney, Agent, or Firm* — Westerman, Hattori, Daniels & Adrian, LLP

(57) ABSTRACT

Concave portions filled with particles of high-absorbent resin are arranged on a side surface of a cylinder part in its circumferential direction. When each concave portion passes about the lowermost portion, the particles are ejected. A first roller conveys a first sheet member so that the first sheet member passes near the above lowermost portion. A second roller is located anterior to the above lowermost portion with respect to a moving direction of the side surface of the cylinder part at the above lowermost portion, and conveys a second sheet member to the vicinity of the above lowermost portion, to place the second sheet member on the first sheet member which has been supplied with particles. In the second roller, annular grooves are formed on the side surface. Therefore, impact on particles which collide with the second sheet member on the second roller is absorbed and scattering of particles is reduced.

3 Claims, 8 Drawing Sheets

(51) Int. Cl.
- *B32B 37/12* (2006.01)
- *B32B 37/24* (2006.01)
- *B32B 37/00* (2006.01)
- *A61F 13/15* (2006.01)
- *B05C 1/08* (2006.01)
- *B05C 1/10* (2006.01)
- *B05C 1/16* (2006.01)
- *B05C 19/00* (2006.01)
- *B05C 19/06* (2006.01)

(52) U.S. Cl.
CPC ....... *A61F13/15804* (2013.01); *B05C 1/0808* (2013.01); *B05C 1/0813* (2013.01); *B05C 1/10* (2013.01); *B05C 1/16* (2013.01); *B05C 19/00* (2013.01); *B05C 19/06* (2013.01)

(56) References Cited

U.S. PATENT DOCUMENTS

| | | | |
|---|---|---|---|
| 5,494,622 A | 2/1996 | Heath et al. | |
| 2006/0021695 A1* | 2/2006 | Blessing | A61F 13/15658 156/196 |
| 2006/0278335 A1* | 12/2006 | Moriura | A61F 13/16568 156/279 |
| 2010/0213231 A1 | 8/2010 | Yamamoto | |

FOREIGN PATENT DOCUMENTS

| | | |
|---|---|---|
| EP | 1621167 A2 | 2/2006 |
| EP | 1655007 A1 | 5/2006 |
| EP | 1700586 A2 | 9/2006 |
| EP | 244044 A1 | 5/2007 |
| JP | 2002-345883 A | 12/2002 |
| JP | 2005-059579 A | 3/2005 |
| JP | 2007-130818 A | 5/2007 |
| JP | 2008-507384 A | 3/2008 |
| KR | 10-2011-0129447 A | 12/2011 |
| WO | 2006/015138 A1 | 2/2006 |
| WO | 2006-015141 A2 | 2/2006 |

OTHER PUBLICATIONS

Written Opinion of PCT/JP2012/004387, mailing date of Oct. 9, 2012.

International Search Report for PCT/JP2012/004389, Mailing Date of Oct. 9, 2012.

Written Opinion for PCTJP2012/004389, Mailing Date of Oct. 9, 2012.

International Search Report, dated Oct. 15, 2012, issued in application No. PCT/JP2012/004386.

Nritten Opinion, dated Oct. 15, 2012, issued in application No. PCT/JP2012/004386.

Notice of Allowance dated Jun. 13, 2016, issued in U.S. Appl. No. 14/130,404, (23 pages).

\* cited by examiner

SHEET ARTICLE MANUFACTURING APPARATUS

TECHNICAL FIELD

The present invention relates to a sheet article manufacturing apparatus for manufacturing a sheet article for an absorbent article.

BACKGROUND ART

Absorbent sheets are conventionally manufactured by supplying a sheet member with particles of high-absorbent resin and placing another sheet member on the above sheet member to bond with each other. For example, in an apparatus of Japanese Patent Application Laid-Open No. 2005-59579 (Document 1), a temporary receiving roller and a transfer roller which are rotated in directions opposite to each other are provided. In the temporary receiving roller, rows of concave grooves arranged on its roller surface at a constant pitch are formed. Each concave groove receives high-absorbent resin particles and holds them in the form of layers. The particles are moved to a position right above a base sheet held on a roller surface of the transfer roller, and the particles are transferred onto a top surface of the base sheet on which hot melt adhesive is applied. In addition, the apparatus of Document 1 is provided with a pressure roller for bonding a cover sheet on the base sheet by pressure bonding. Immediately after the base sheet on which the high-absorbent resin particle layer has been transferred comes through a gap between the temporary receiving roller and the transfer roller, the base sheet is covered with the cover sheet.

Incidentally, in a case like the apparatus of Document 1, a plurality of concave portions each filled with particles of high-absorbent resin are arranged on an outer side surface of a cylinder part in a circumferential direction, and the cylinder part is rotated to sequentially eject the particles onto a first sheet member. In the above case, it is preferable that immediately after each portion of the first sheet member is supplied with particles, a second sheet member is placed on the portion to hold the particles between the sheet members. In this case, a sheet conveying roller for conveying the second sheet member needs to be located in the vicinity of a particle supply position. However some of particles ejected from the cylinder part collide with an outer side surface of the sheet conveying roller through the second sheet member and as a result, some particles are scattered around and wasted. Therefore, a technique of reducing scattering of particles is required.

SUMMARY OF INVENTION

The present invention is intended for a sheet article manufacturing apparatus for manufacturing a sheet article for an absorbent article. It is an object of the present invention to reduce scattering of particles ejected toward a sheet member.

The sheet article manufacturing apparatus according to the present invention comprises: a cylinder part having an outer side surface which is generally cylindrical around a rotation axis along a horizontal direction, a plurality of holes each filled with particles of absorbent material or deodorant material being arranged on the outer side surface in a circumferential direction around the rotation axis, the outer side surface being rotated around the rotation axis in a predetermined rotation direction, the cylinder part ejecting the particles almost along a tangent line of the outer side surface at an ejection start position when each of the plurality of holes passes the ejection start position, the ejection start position being set in a vicinity of a lowermost portion in a cross section of the outer side surface which is orthogonal to the rotation axis; a first sheet conveying roller which is located near the lowermost portion of the cylinder part, the first sheet conveying roller having an outer side surface which is generally cylindrical around a first central axis parallel to the rotation axis, the outer side surface being rotated around the first central axis in a rotation direction opposite to the rotation direction of the cylinder part to convey a first sheet member along the outer side surface which is continuous sheet and cause the first sheet member to pass in the vicinity of the lowermost portion of the cylinder part; a second sheet conveying roller which is located anterior to the lowermost portion of the cylinder part with respect to a moving direction of the outer side surface at the lowermost portion, the second sheet conveying roller having an outer side surface which is generally cylindrical around a second central axis parallel to the rotation axis, for conveying a second sheet member along the outer side surface to the vicinity of the lowermost portion to place the second sheet member on the first sheet member which has been supplied with the particles, the second sheet member being continuous sheet; and a sheet bonding part for bonding the second sheet member on the first sheet member; wherein the second sheet conveying roller has a groove or an absorber on the outer side surface, the groove extending along substantially the entire length of the outer side surface in a circumferential direction around the second central axis and facing holes of the cylinder part, the absorber being configured to absorb impact on the particles which collide with the second sheet member on the outer side surface.

In the present invention, it is possible to reduce scattering of particles by absorbing impact on particles which collide with the second sheet member on the second sheet conveying roller.

According to a preferred embodiment of the present invention, the second sheet conveying roller has an annular groove as the above groove, the annular groove being formed on the outer side surface along a circumferential direction around the second central axis. In this case, preferably, the plurality of holes are formed on the outer side surface of the cylinder part with respect to each of a plurality of positions in an axial direction parallel to the rotation axis, and the annular groove is formed on the outer side surface of the second sheet conveying roller with respect to each of the plurality of positions in the axial direction. More preferably, the sheet article manufacturing apparatus further comprises an applying part for applying adhesive onto a plurality of strip-like regions lying on the first sheet member, the plurality of strip-like regions corresponding to the plurality of positions in the axial direction. As a result, particles can be accurately fixed on the plurality of strip-like regions of a sheet article for an absorbent article.

These and other objects, features, aspects and advantages of the present invention will become more apparent from the following detailed description of the present invention when taken in conjunction with the accompanying drawings.

DESCRIPTION OF EMBODIMENTS

Figure 1:
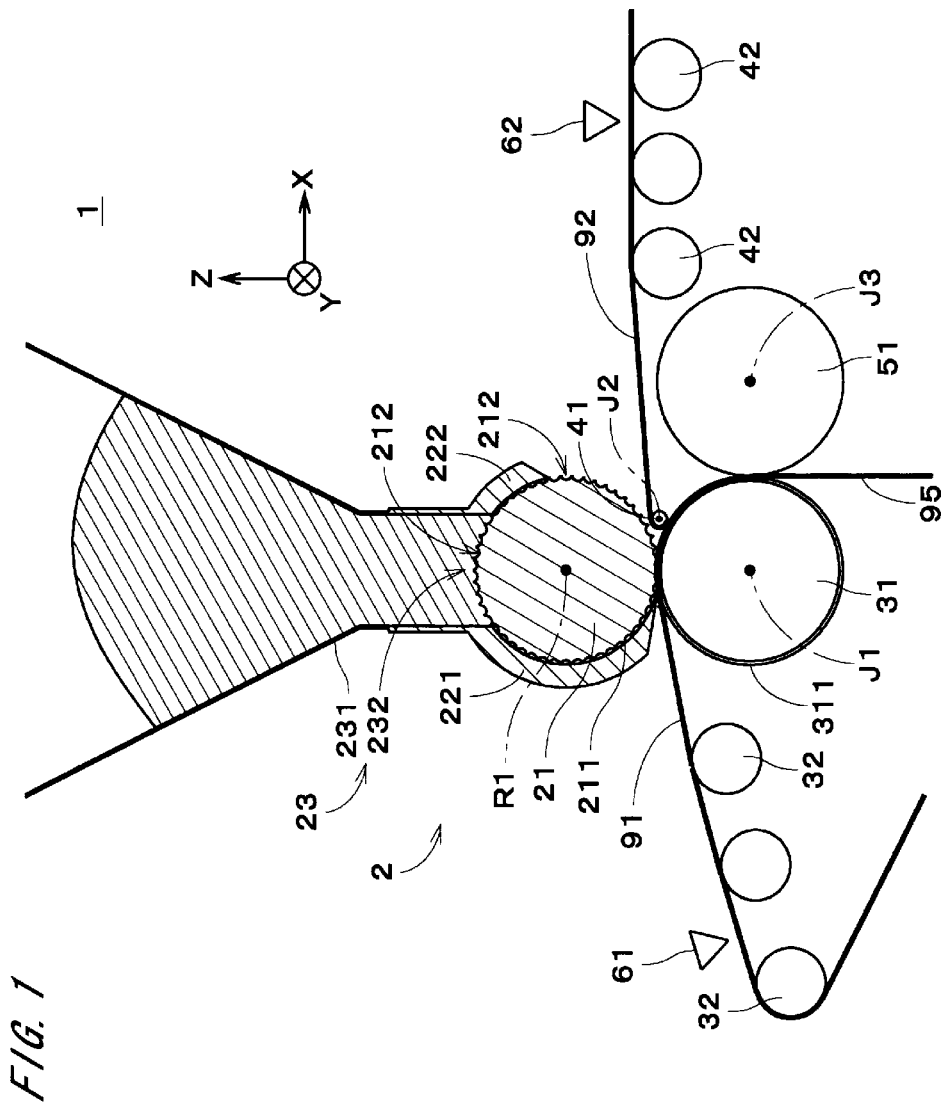
FIG. 1 is a view showing a structure of an absorbent sheet manufacturing apparatus.

FIG. 1 is a view showing a structure of an absorbent sheet manufacturing apparatus 1 in accordance with a preferred embodiment of the present invention. The absorbent sheet manufacturing apparatus 1 is one sheet article manufacturing apparatus for manufacturing a sheet article for an absorbent article and manufactures absorbent sheets by sandwiching particles of high-absorbent resin such as SAP (Super Absorbent Polymer) between sheet members formed of nonwoven fabric or the like. The absorbent sheet is a sheet article used for an absorbent article such as a disposable diaper or absorbent pad for light incontinence.

The absorbent sheet manufacturing apparatus 1 has a cylinder part 21 having a generally columnar shape around (with its center lying on) a rotation axis R1 parallel to a predetermined axial direction (the Y direction in FIG. 1) along a horizontal direction, a first sheet conveying roller 31 having a generally columnar shape around a first central axis J1 parallel to the axial direction, a second sheet conveying roller 41 having a generally columnar shape around a second central axis J2 parallel to the axial direction, and a bonding roller 51 having a generally columnar shape around a third central axis J3 parallel to the axial direction. In FIG. 1, another horizontal direction orthogonal to the axial direction is shown as the X direction, and the vertical direction (i.e., direction of gravitational force) orthogonal to the X direction and the Y direction is shown as the Z direction.

The cylinder part 21, the second sheet conveying roller 41 and the bonding roller 51 are rotated in a counterclockwise direction in FIG. 1, and the first sheet conveying roller 31 is rotated in a clockwise direction in FIG. 1. The first sheet conveying roller 31 is located under (on the (−Z) side of) the cylinder part 21 and conveys a first sheet member 91 formed of nonwoven fabric or the like to cause the first sheet member 91 to pass under a lowermost portion (i.e., an outermost portion on the (−Z) side) of the cylinder part 21. The second sheet conveying roller 41 has a smaller diameter than those of the cylinder part 21 and the first sheet conveying roller 31, and is located in the vicinity of the lowermost portion of the cylinder part 21. The second sheet conveying roller 41 conveys a second sheet member 92 formed of nonwoven fabric or the like to the vicinity of the lowermost portion of the cylinder part 21. The bonding roller 51 is provided beside the first sheet conveying roller 31.

The cylinder part 21 has an outer side surface 211 which is a generally cylindrical surface around the rotation axis R1. A first cover part 221 which covers a portion of the outer side surface 211 and a second cover part 222 which covers another portion of the outer side surface 211 are provided around the cylinder part 21. In FIG. 1, the cylinder part 21, the first cover part 221, the second cover part 222 and an after-mentioned particle filling part 23 are shown as cross sections which are orthogonal to the rotation axis R1.

Figure 2:
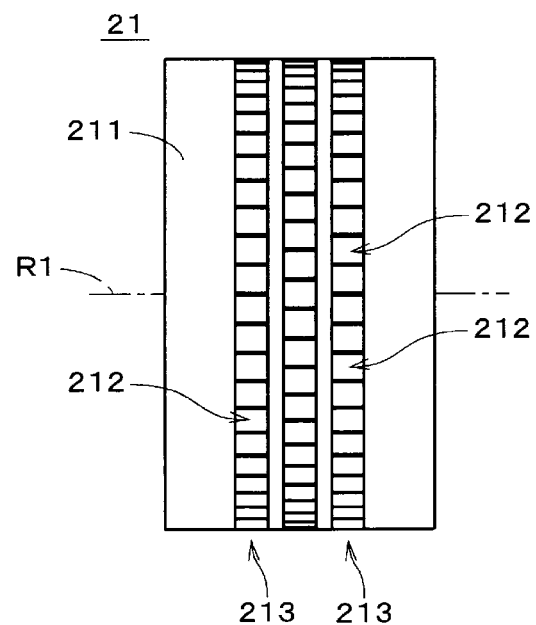
FIG. 2 is a view showing an outer side surface of a cylinder part.

FIG. 2 is a view showing the outer side surface 211 of the cylinder part 21, and in FIG. 2, an appearance of the outer side surface 211 of the cylinder part 21 which is observed along a direction orthogonal to the rotation axis R1 is shown. In FIG. 2, the first and second cover parts 221, 222 are omitted. A plurality of concave portions 212 are arranged on (in) the outer side surface 211 of the cylinder part 21 in a circumferential direction around the rotation axis R1 with respect to each of a plurality of positions in the axial direction. When the plurality of concave portions 212 which are arranged in the circumferential direction at the same position in the axial direction are referred to as a concave portion row 213, three concave portion rows 213 are formed in the cylinder part 21 shown in FIG. 2. In FIG. 2, a shape of opening of each concave portion 212 which is a hole is generally rectangular, however the aperture may have a various shape (for example, generally circular shape).

As shown in FIG. 1, a particle filling part 23 storing particles of high-absorbent resin is provided above the cylinder part 21, and the particle filling part 23 fills the plurality of concave portions 212 of the cylinder part 21 with the particles. The particle filling part 23 has a particle tank 231 storing the particles, and a particle filling opening 232 facing the outer side surface 211 of the cylinder part 21 is provided under the particle tank 231. A not-shown level sensor is provided to the particle tank 231, and therefore particles are replenished into the particle tank 231 when the amount of particles stored in the particle tank 231 becomes equal to or less than a certain level.

The outer side surface 211 of the cylinder part 21 is rotated around the rotation axis R1 at a high speed in the counterclockwise direction in FIG. 1 by a not-shown motor, and particles are filled into each concave portion 212 passing the particle filling opening 232, by gravity. The first cover part 221 spreads from the particle filling part 23 toward the anterior side (downstream side) in the rotation direction of the cylinder part 21. Each concave portion 212 is closed (blocked) with the first cover part 221 after passing the particle filling part 23 until reaching the vicinity of the lowermost portion of the cylinder part 21. When each concave portion 212 passes the tip of the first cover part 221 (i.e., one end in the vicinity of the lowermost portion of the cylinder part 21), the particles in the concave portion 212 are ejected. As described later, particles ejected from the concave portion 212 are held on the first sheet member 91. In the following description, a position of the tip of the first cover part 221 in a cross section of the outer side surface 211 which is orthogonal to the rotation axis R1 is referred to as an "ejection start position". Details of ejection of particles from the cylinder part 21 will be discussed later.

The second cover part 222 spreads from the particle filling part 23 toward the posterior side (upstream side) in the rotation direction of the cylinder part 21. Each concave portion 212 which has ejected particles is closed with the second cover part 222 immediately before reaching the particle filling part 23. In the absorbent sheet manufacturing apparatus 1, the cylinder part 21, the first cover part 221, the second cover part 222 and the particle filling part 23 construct a particle supplying part 2 for supplying particles of high-absorbent resin onto the first sheet member 91.

Figure 3:
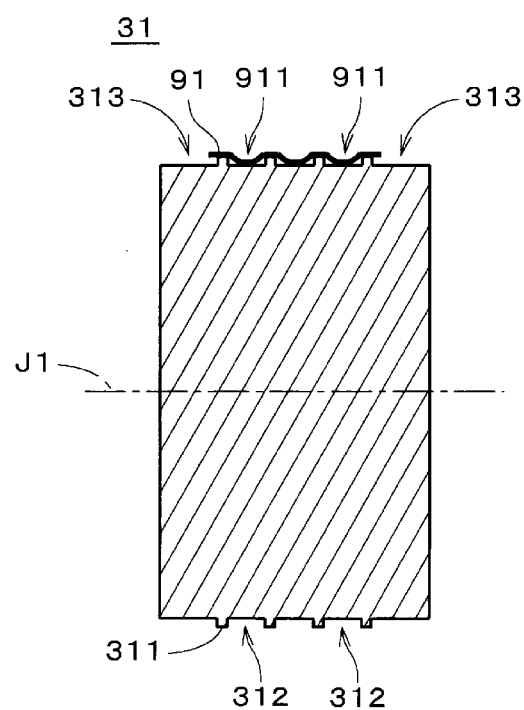
FIG. 3 is a cross-sectional view of a first sheet conveying roller.

FIG. 3 is a cross-sectional view of the first sheet conveying roller 31 and shows a cross section of the first sheet conveying roller 31 taken along a plane including the rotation axis R1 of the cylinder part 21 in FIG. 1 and the first central axis J1 of the first sheet conveying roller 31. The first sheet conveying roller 31 shown in FIG. 1 is located in the vicinity of the lowermost portion of the cylinder part 21. As shown in FIG. 3, the first sheet conveying roller 31 has an outer side surface 311 which is a generally cylindrical surface around the first central axis J1, and an annular groove 312 along a circumferential direction around the first central axis J1 is formed on (in) the outer side surface 311 with respect to each of the plurality of positions in the axial direction. The plurality of annular grooves 312 face the plurality of concave portion rows 213 of the cylinder part 21, respectively (that is, the annular grooves 312 are disposed at same positions in the axial direction as the positions of the concave portion rows 213). Annular cutout portions 313 are formed at both end portions in the axial direction on the outer side surface 311 of the first sheet conveying roller 31 in FIG. 3. The cutout portions 313 are not necessarily provided.

Figure 4:
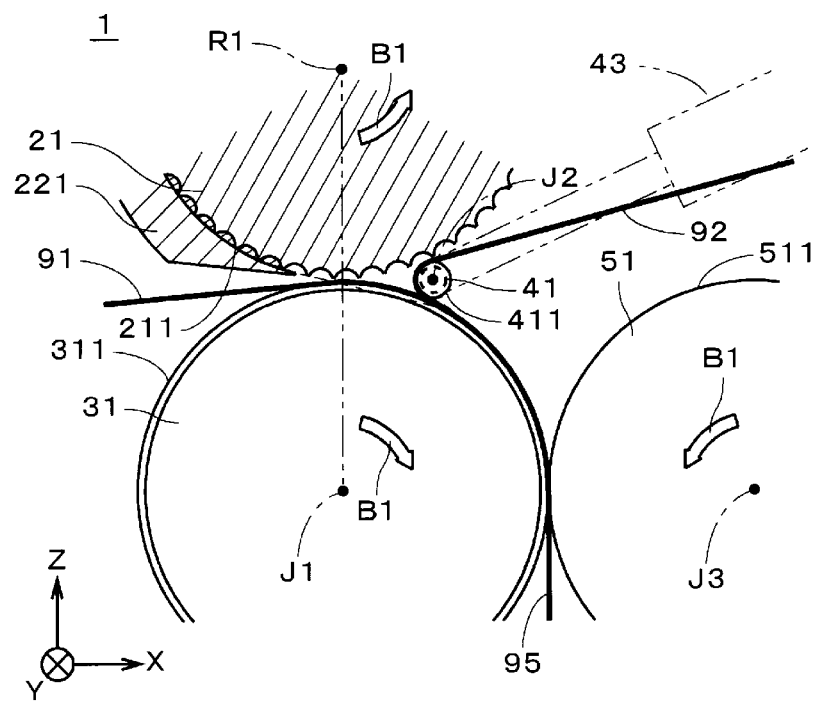
FIG. 4 is a view showing a vicinity of a lowermost portion of the cylinder part.

FIG. 4 is an enlarged view showing the vicinity of the lowermost portion of the cylinder part 21 in FIG. 1. In FIG. 4, the rotation directions of the cylinder part 21, the first sheet conveying roller 31 and the bonding roller 51 are shown by arrows denoted by a reference sign B1 (the same applies to after-mentioned FIG. 10). The outer side surface 311 of the first sheet conveying roller 31 is slightly away from the outer side surface 211 of the cylinder part 21, and the outer side surface 311 is rotated around the first central axis J1 in the rotation direction (in the clockwise direction in FIG. 4) opposite to the rotation direction of the cylinder part 21 as mentioned previously. The first sheet member 91 which is continuous sheet is led to the first sheet conveying roller 31 through a plurality of auxiliary rollers 32 (see FIG. 1), to be conveyed continuously along the outer side surface 311 of the first sheet conveying roller 31. At this time, the first sheet member 91 passes the vicinity of the lowermost portion of the cylinder part 21, and particles ejected from the cylinder part 21 are held on one main surface thereof. The movement speed of the outer side surface 211 at the lowermost portion of the cylinder part 21 is different from (or may be same as) the movement speed of the outer side surface 311 at the uppermost portion of the first sheet conveying roller 31.

Figure 5:
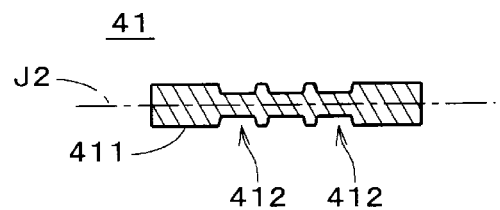
FIG. 5 is a cross-sectional view of a second sheet conveying roller.

FIG. 5 is a cross-sectional view of the second sheet conveying roller 41 and shows a cross section of the second sheet conveying roller 41 taken along a plane including the second central axis J2 of the second sheet conveying roller 41 in FIG. 4. With respect to a moving direction (the X direction in FIG. 1) of the outer side surface 211 of the cylinder part 21 at the lowermost portion, the second sheet conveying roller 41 shown in FIG. 4 lies anterior to the lowermost portion. As shown in FIG. 5, the second sheet conveying roller 41 has an outer side surface 411 which is a generally cylindrical surface around the second central axis J2, and an annular groove 412 along a circumferential direction around the second central axis J2 is formed on the outer side surface 411 with respect to each of the plurality of positions in the axial direction. The plurality of annular grooves 412 face the plurality of the concave portion rows 213 of the cylinder part 21 (and the plurality of annular grooves 312 of the first sheet conveying roller 31), respectively.

As mentioned previously, since the diameter of the second sheet conveying roller 41 in FIG. 4 is sufficiently-small in comparison with those of the cylinder part 21 and the first sheet conveying roller 31, the second sheet conveying roller 41 can be easily located in the vicinity of the lowermost portion of the cylinder part 21. In addition, the outer side surface 411 of the second sheet conveying roller 41 is rotated around the second central axis J2 in the counterclockwise direction in FIG. 1. The second sheet member 92 which is continuous sheet is led to the second sheet conveying roller 41 through a plurality of auxiliary rollers 42 (see FIG. 1), to be conveyed continuously along the outer side surface 411 of the second sheet conveying roller 41. Then, the second sheet member 92 is placed (stacked) on the first sheet member 91 which has passed under the lowermost portion of the cylinder part 21. The second sheet conveying roller 41 can be moved between the position shown in FIG. 4 and a position on the (+X) side of the cylinder part 21 by a forward/backward moving mechanism 43 shown by chain double-dashed lines in FIG. 4.

Figure 6:
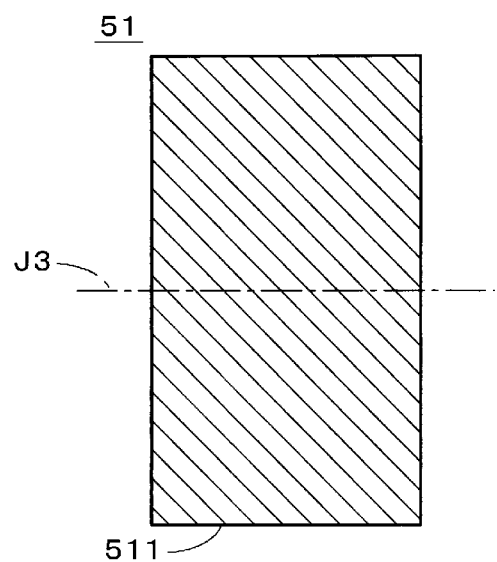
FIG. 6 is a cross-sectional view of a bonding roller.

FIG. 6 is a cross-sectional view of the bonding roller 51 and shows a cross section of the bonding roller 51 taken along a plane including the third central axis J3 of the bonding roller 51 in FIG. 4. As shown in FIG. 6, the bonding roller 51 has an outer side surface 511 which is a cylindrical surface around the third central axis J3, the outer side surface 511 is a smooth surface. As shown in FIG. 4, the first sheet member 91 and the second sheet member 92 overlaid with each other are placed (sandwiched) between the outer side surface 311 of the first sheet conveying roller 31 and the outer side surface 511 of the bonding roller 51. The both (or one) of the first sheet conveying roller 31 and the bonding roller 51 are provided with heaters, and regions of the first sheet member 91 and the second sheet member 92 which come into contact with the outer side surface 311 of the first sheet conveying roller 31 (i.e., portions of the outer side surface except for the annular grooves 312 and the cutout portions 313) are heat-sealed with each other, so that the first sheet member 91 and the second sheet member 92 are bonded with each other.

As shown in FIG. 1, the absorbent sheet manufacturing apparatus 1 further has a first applying part 61 for applying adhesive (in the present embodiment, hot melt adhesive) onto the first sheet member 91 and a second applying part 62 for applying same adhesive onto the second sheet member 92. The first applying part 61 is located upstream of the first sheet conveying roller 31 in a conveyance path of the first sheet member 91. In the first applying part 61, the adhesive is applied onto only a plurality of strip-like regions on the first sheet member 91 whose positions are identical to the positions of the plurality of concave portion rows 213 (and the plurality of annular grooves 312) with respect to the axial direction. The second applying part 62 is located upstream of the second sheet conveying roller 41 in a conveyance path of the second sheet member 92. In the second applying part 62, the adhesive is applied onto only a plurality of strip-like regions on the second sheet member 92 whose positions are identical to the positions of the plurality of concave portion rows 213 with respect to the axial direction.

Figure 7:
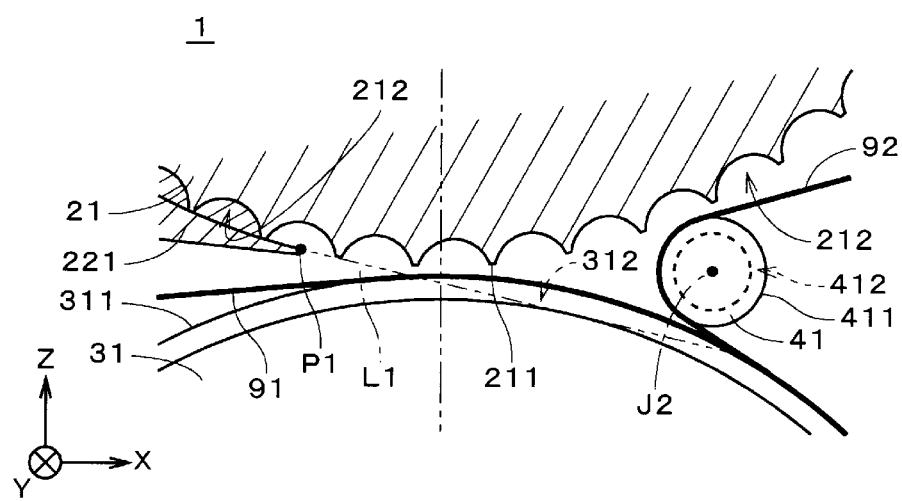
FIG. 7 is an enlarged view showing the vicinity of the lowermost portion of the cylinder part.

Next, the details of ejection of particles from the cylinder part 21 will be discussed. FIG. 7 is a further enlarged view showing the vicinity of the lowermost portion of the cylinder part 21 in FIG. 4. As shown in FIG. 7, in the cross section of the outer side surface 211 of the cylinder part 21 which is orthogonal to the axial direction, the ejection start position P1 in the vicinity of the lowermost portion of the cylinder part 21 is set at a position lying posterior to (upstream of) the lowermost portion in the rotation direction. As mentioned previously, the cylinder part 21 is rotated at a high speed. Thus, when each of the plurality of concave portions 212 passes the ejection start position P1 (actually, during the passage and immediately after the passage), particles are ejected from the concave portion 212 almost along a tangent line of the outer side surface 211 at the ejection start position P1 (the tangent line is shown in FIG. 7 by a chain double-dashed line denoted by a reference sign L1). In other words, the rotation speed of the cylinder part 21, the shape of the concave portion 212 and the like are determined so that the particles are ejected from the concave portion 212 almost along the tangent line L1 (for example, the particles go toward a direction included in an angle range from (+15) degree to (−15) degree with respect to the tangent line L1 (preferably, from (+10) degree to (−10) degree)). For example, the movement speed of the outer side surface 211 in the direction of the tangent line L1 is 200 meters per minute.

At this time, the tangent line L1 intersects with the outer side surface 311 of the first sheet conveying roller 31, and the positions of the annular grooves 312 of the first sheet conveying roller 31 are identical to the positions of the plurality of concave portion rows 213 with respect to the axial direction (see FIG. 2). Therefore most particles ejected from each concave portion 212 go toward the correspondent annular groove 312. At an intersection point between the tangent line L1 and the outer side surface 311, the first sheet member 91 is in contact with the outer side surface 311.

In the first sheet conveying roller 31, a diameter of the outer side surface 311 is comparatively-large and also the first sheet member 91 is stretched along the outer side surface 311 at a certain tension. Therefore, as shown in FIG. 3, each portion 911 of the first sheet member 91 corresponding to the annular groove 312 becomes a shape depressed toward the bottom of the annular groove 312. In other words, groove portions 911 corresponding to the annular grooves 312 are formed on the first sheet member 91. Thus, the particles ejected from the concave portions 212 of the cylinder part 21 toward the insides of the annular grooves 312 are received (caught) in the groove portions 911. At this time, even if particles bounce from the first sheet member 91 in the groove portions 911, scattering of particles to the outside of the groove portions 911 is suppressed (reduced) by side walls of the groove portions 911. In addition, since adhesive is applied onto the plurality of strip-like regions on the first sheet member 91 whose positions are same as those of the plurality of annular grooves 312 with respect to the axial direction, particles are easily caught in the groove portions 911.

Some particles bounce from the first sheet member 91 in the groove portions 911 to go toward the second sheet conveying roller 41 shown in FIG. 7 (in fact, their flying speeds are decreased by shock absorption by the first sheet member 91), and others go from the concave portions 212 of the cylinder part 21 to the second sheet conveying roller 41 directly. As mentioned previously, in the second sheet conveying roller 41, the plurality of annular grooves 412 are formed whose positions are same as those of the plurality of concave portion rows 213 with respect to the axial direction, and the particles heading to the second sheet conveying roller 41 collide with portions of the second sheet member 92 lying right above the annular grooves 412 (i.e., the portions at which the back surface is not in contact with any substance), so that the impact is absorbed. As a result, some particles are falls into the groove portions 911 of the first sheet member 91 to be collected therein, and others adhere to the surface of the second sheet member 92 where adhesive is applied.

As mentioned previously, immediately after portions on the first sheet member 91 are supplied with particles, the second sheet member 92 is placed on the portions by the second sheet conveying roller 41 in the vicinity of the lowermost portion of the cylinder part 21. Subsequently the first sheet member 91 and the second sheet member 92 are bonded with each other by the bonding roller 51 in FIG. 4 which is a sheet bonding part, to complete the absorbent sheet 95. As above, the second sheet conveying roller 41 and the bonding roller 51, which function as a conveying and bonding part, work harmoniously with the first sheet conveying roller 31, to thereby place and bond the second sheet member 92 on the first sheet member 91.

Figure 8:
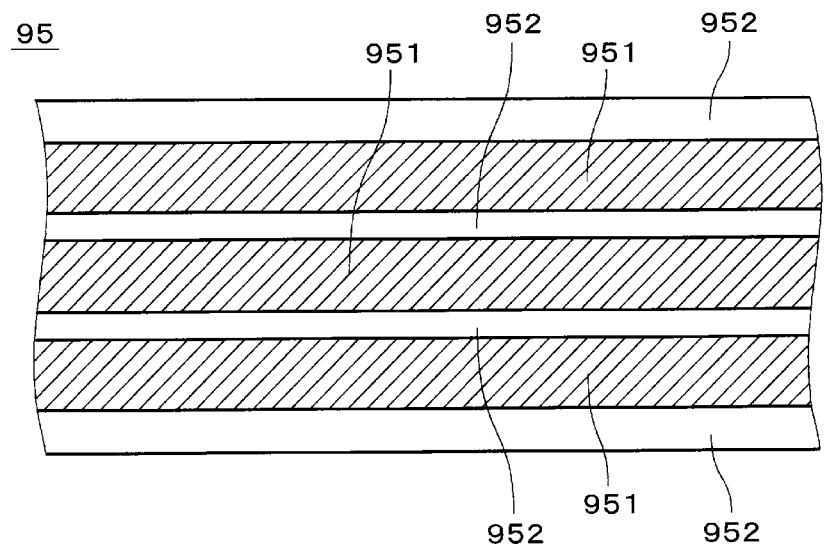
FIG. 8 is a view showing an absorbent sheet.

FIG. 8 is a view showing the absorbent sheet 95 manufactured by the absorbent sheet manufacturing apparatus 1. In the absorbent sheet 95, a plurality of particle existence regions 951 and a plurality of particle non-existence regions 952 are alternately arranged in the width direction. The plurality of particle existence regions 951 are strip-like (or linear) regions where particles of high-absorbent resin are held (in FIG. 8, hatching lines are drawn at the regions), and the plurality of particle non-existence regions 952 are strip-like regions where particles don't exist essentially and the first sheet member 91 and the second sheet member 92 are bonded with each other. In other words, the plurality of particle existence regions 951 are provided in a stripe state in the absorbent sheet 95. In fact, members obtained by cutting the absorbent sheet 95 into same length pieces with respect to the longitudinal direction are used as absorbent parts for absorbent articles. In absorbent articles having such absorbent parts, since adhesive isn't applied on the particle non-existence regions 952, air permeability (breathability) is improved. In order to close both ends of the particle existence regions 951, in each end portion of the member in the longitudinal direction, both sheet members are bonded with each other across the entire length in the width direction, if necessary.

Figure 9:
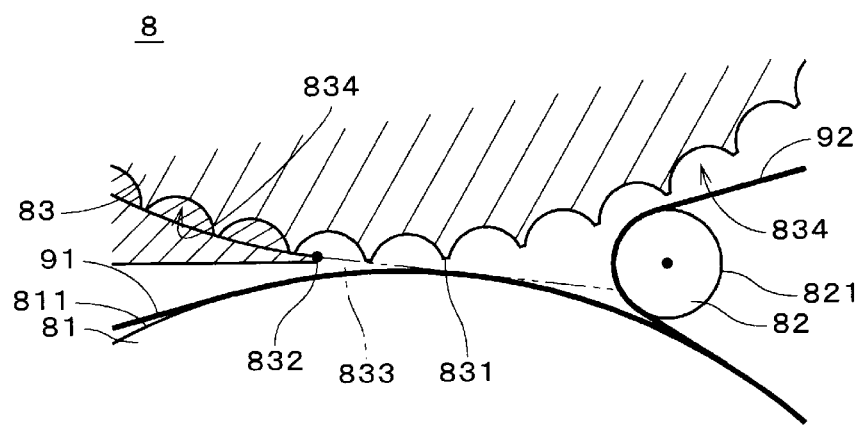
FIG. 9 is a view showing a comparative example of absorbent sheet manufacturing apparatus.

Here, discussion will be made on a comparative example of absorbent sheet manufacturing apparatus. FIG. 9 is a view showing parts of an absorbent sheet manufacturing apparatus 8 in accordance with a comparative example and FIG. 9 corresponds to FIG. 7. In the absorbent sheet manufacturing apparatus 8 of the comparative example, any annular grooves are not formed on the first sheet conveying roller 81 and the second sheet conveying roller 82. In addition, a tangent line (shown in FIG. 9 by a chain double-dashed line denoted by a reference sign 833) of the outer side surface 831 of the cylinder part 83 at the ejection start position 832 doesn't intersect with the outer side surface 811 of the first sheet conveying roller 81. In the absorbent sheet manufacturing apparatus 8 of the comparative example, particles are ejected from the concave portion 834 of the cylinder part 83 almost along the tangent line 833, and some particles go toward the second sheet conveying roller 82. These particles collide with the outer side surface 821 of the second sheet conveying roller 82 through the second sheet member 92 (i.e., collide with the second sheet member 92 held on the second sheet conveying roller 82), to be widely scattered around. Also particles heading to the first sheet conveying roller 81 collide with the outer side surface 811 of the first sheet conveying roller 81 through the first sheet member 91, to be widely scattered around. As above, in the absorbent sheet manufacturing apparatus 8 of the comparative example, scattered particles are wasted and manufacturing cost of the absorbent sheets is increased. In addition, it is difficult to accurately fix particles on regions of the absorbent sheets corresponding to the concave portion rows of the cylinder part 83.

In contrast to this, on the outer side surface 311 of the first sheet conveying roller 31 in the absorbent sheet manufacturing apparatus 1 of FIG. 7, the plurality of annular grooves 312 are formed at positions, respectively, which are identical to the positions of the plurality of concave portion rows 213 of the cylinder part 21 with respect to the axial direction. In addition, the tangent line L1 of the outer side surface 211 at the ejection start position P1 in the cylinder part 21 intersects with the outer side surface 311 of the first sheet conveying roller 31. It is therefore possible to eject particles from the cylinder part 21 into the groove portions 911 of the first sheet member 91 and reduce (suppress) scattering of particles, and as a result, particles can be accurately fixed (settled) on the strip-like regions (particle existence regions 951) of the absorbent sheet 95 corresponding to the annular grooves 312.

The second sheet conveying roller 41 has the annular grooves 412 which extend along substantially the entire length of the outer side surface 411 in the circumferential direction around the second central axis J2 and which face the concave portions 212 of the cylinder part 21. This makes it possible to absorb impact on particles which collide with the second sheet member 92 on the second sheet conveying roller 41, to reduce scattering of particles (the same applies to examples of after-mentioned FIGS. 10 to 13). Since waste of particles can be reduced in the absorbent sheet manufacturing apparatus 1, manufacturing cost of the absorbent sheet can be reduced. Furthermore, adhesive is applied onto only the plurality of strip-like regions on the first sheet member 91. This allows particles to be more accurately fixed on the plurality of strip-like regions (particle existence regions 951) of the absorbent sheet 95.

Figure 10:
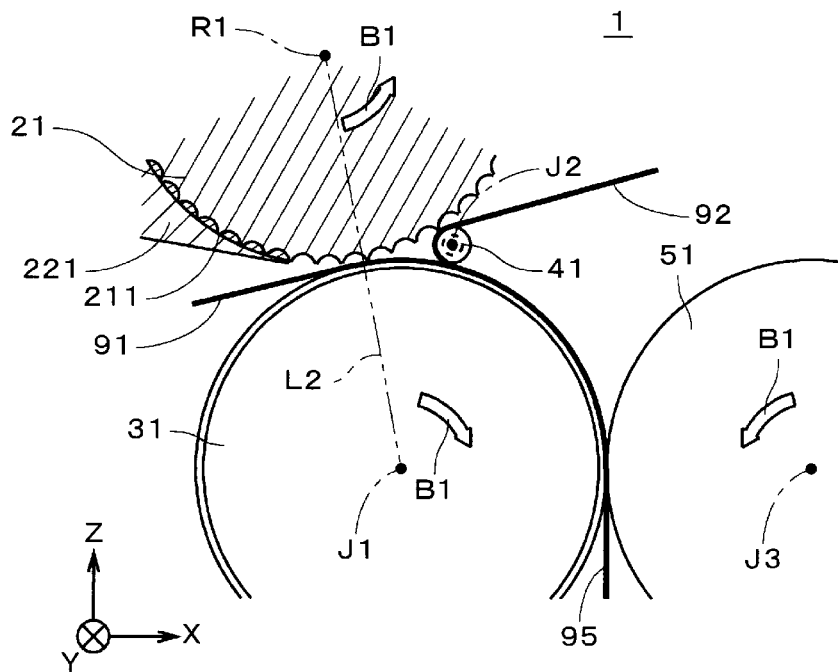
FIG. 10 is a view showing another example of absorbent sheet manufacturing apparatus.

FIG. 10 is a view showing another example of absorbent sheet manufacturing apparatus and FIG. 10 corresponds to FIG. 4. In an absorbent sheet manufacturing apparatus 1 in accordance with another example, with respect to a moving direction (the X direction in FIG. 10) of the outer side surface 211 of the cylinder part 21 at the lowermost portion, the first central axis J1 of the first sheet conveying roller 31 lies anterior to (on the (+X) side of) the rotation axis R1 of the cylinder part 21. In fact, the position of the particle supplying part 2 shown in FIG. 1 is slightly moved leftward and downward (toward the (−X) side and (−Z) side) in FIG. 1 relative to the other members, and then the position of the second sheet conveying roller 41 is adjusted so that the relative position of the second central axis J2 of the second sheet conveying roller 41 with respect to the rotation axis R1 of the cylinder part 21 and the first central axis J1 of the first sheet conveying roller 31 becomes same as that in FIG. 1. Therefore, the cylinder part 21, the first sheet conveying roller 31 and the second sheet conveying roller 41 are located at positions shown in FIG. 10. In the absorbent sheet manufacturing apparatus 1 in FIG. 10, a state where the particle filling opening 232 (see FIG. 1) is parallel to the horizontal plane is maintained. In addition, if necessary, the positions of the plurality of auxiliary rollers 32 (see FIG. 1) are adjusted so that a line segment L2 (shown in FIG. 10 by a chain double-dashed line) connecting the rotation axis R1 of the cylinder part 21 and the first central axis J1 of the first sheet conveying roller 31 becomes almost orthogonal to the first sheet member 91.

Figure 11:
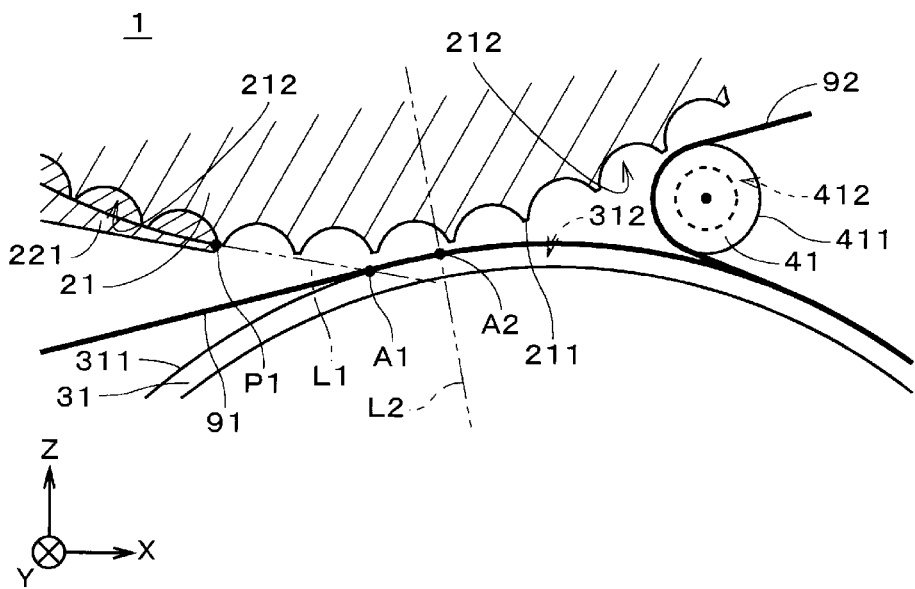
FIG. 11 is an enlarged view showing a vicinity of a lowermost portion of a cylinder part.

FIG. 11 is an enlarged view showing the vicinity of the lowermost portion of the cylinder part 21 in FIG. 10 and FIG. 11 corresponds to FIG. 7. As shown in FIG. 11, in an absorbent sheet manufacturing apparatus 1 in accordance with another example, the position of the first cover part 221 is adjusted so that a position at which the tangent line L1 of the outer side surface 211 at the ejection start position P1 in the cylinder part 21 intersects with a bottom surface of an annular groove 312 of the first sheet conveying roller 31 lies on the (−X) side of the uppermost portion of the first sheet conveying roller 31. Thus, particles directly heading toward the second sheet conveying roller 41 from the cylinder part 21 are decreased in particles ejected from the cylinder part 21.

In addition, in the absorbent sheet manufacturing apparatus 1 of FIG. 11, a first intersection point A1 at which the above tangent line L1 intersects with the outer side surface 311 of the first sheet conveying roller 31 lies posterior to (upstream of) a second intersection point A2 in the rotation direction of the first sheet conveying roller 31, at which the above line segment L2 intersects with the outer side surface 311 of the first sheet conveying roller 31. Thus, particles are ejected toward the vicinity of the posterior side, in the rotation direction of the first sheet conveying roller 31, of the portion (the portion in the vicinity of the second intersection point A2) which is nearest to the outer side surface 211 of the cylinder part 21, in the outer side surface 311 of the first sheet conveying roller 31. Therefore, even if particles bounce from the first sheet member 91 in the annular grooves 312, scattering of particles can be suppressed by portions of the outer side surface 211 of the cylinder part 21 which are near (close to) the first sheet conveying roller 31, and particles can be more accurately fixed on the strip-like regions of the absorbent sheet 95 corresponding to the annular grooves 312.

In the absorbent sheet manufacturing apparatus 1 of FIG. 4, by rotating the first cover part 221 posteriorly (clockwise) in the rotation direction of the cylinder part 21 around the rotation axis R1 by a predetermined angle, the first intersection point at which the tangent line of the outer side surface 211 at the ejection start position (the tip of the first cover part 221) intersects with the outer side surface 311 of the first sheet conveying roller 31 can lie posterior to the second intersection point in the rotation direction of the first sheet conveying roller 31, at which the line segment connecting the rotation axis R1 and the first central axis J1 intersects with the outer side surface 311. However, it is preferable that the position of the first central axis J1 of the first sheet conveying roller 31 and the position of the rotation axis R1 of the cylinder part 21 are displaced in the X direction like the absorbent sheet manufacturing apparatus 1 in FIG. 10, in order to eject particles almost along a horizontal direction at the ejection start position (for example, if an angle formed between the tangent line of the outer side surface 211 at the ejection start position and the X direction is made equal to or less than 30 degree).

Figure 12:
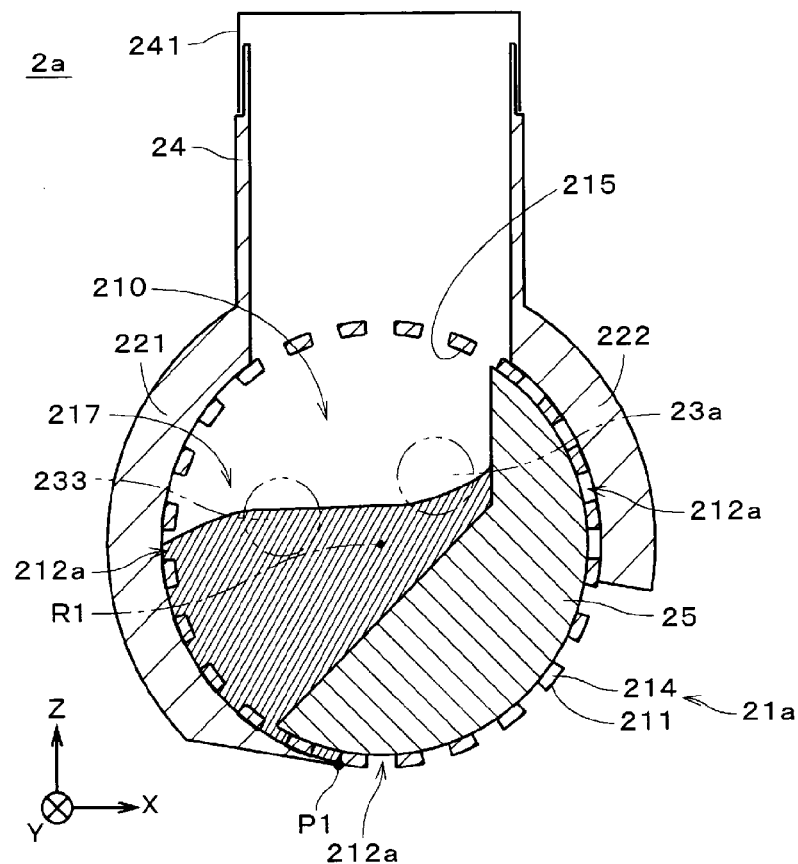
FIG. 12 is a view showing another example of particle supplying part.

Although particles are ejected from the concave portions 212 on the outer side surface 211 toward the first sheet member 91 in the particle supplying part 2 of FIG. 1, another particle supplying part may be utilized in the absorbent sheet manufacturing apparatus 1. FIG. 12 is a view showing another example of particle supplying part.

In the particle supplying part 2a of FIG. 12, the cylinder part 21a is a generally cylindrical member around the rotation axis R1 and has a ring-like side wall 214. A cylindrical exhaust part 24 is provided above the cylinder part 21a as substitute for the particle filling part 23 in FIG.

1, and a pouched filter 241 formed of nonwoven fabric or the like is attached to an upper portion of the exhaust part 24. The first cover part 221 and the second cover part 222 similar to those in FIG. 1 are provided around the cylinder part 21*a*.

Figure 13:
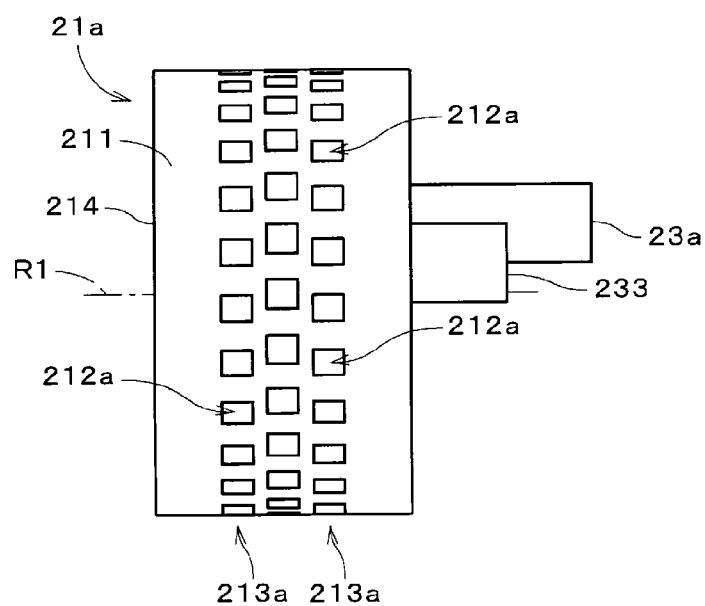
FIG. 13 is a view showing an outer side surface of a cylinder part.

FIG. 13 is a view showing an outer side surface 211 of the side wall 214 of the cylinder part 21*a*, and in FIG. 13, an appearance of the outer side surface 211 which is observed along a direction orthogonal to the rotation axis R1 is shown. In FIG. 13, the first and second cover parts 221, 222 are omitted. As shown in FIGS. 12 and 13, the cylinder part 21*a* has a plurality of through-holes 212*a* which are holes passing through the side wall 214. The plurality of through-holes 212*a* are arranged in the circumferential direction around the rotation axis R1 with respect to each of a plurality of positions in the axial direction. When the plurality of through-holes 212*a* which are arranged in the circumferential direction at the same position in the axial direction are referred to as a through-hole row 213*a*, three through-hole rows 213*a* are provided in the cylinder part 21*a* shown in FIG. 13.

As shown in FIG. 12, an isolation part 25 which covers a portion of an inner side surface 215 of the side wall 214 of the cylinder part 21*a* is provided in the internal space 210 of the cylinder part 21*a*. The isolation part 25 is provided in the right portion of the internal space 210 in FIG. 12 and covers the right portion of the inner side surface 215 from the vicinity of the lowermost portion of the cylinder part 21*a* to the vicinity of the uppermost portion. The isolation part 25 faces a portion of the side wall 214 positioned from the lower end portion of the first cover part 221 to the upper end portion of the second cover part 222 with respect to the rotation direction of the cylinder part 21*a* (in the counter-clockwise direction in FIG. 12). In the cylinder part 21*a*, a portion of the internal space 210 where the isolation part 25 doesn't exist is a particle storage space 217 which stores particles of high-absorbent resin. The isolation part 25 is provided across almost the entire width of the inner side surface 215 of the cylinder part 21*a* in the axial direction, so that through-holes 212*a* in a region of the inner side surface 215 which is covered with the isolation part 25 are isolated from the particle storage space 217. Thus, also in a region of the inner side surface 215 which is from the tip of the first cover part 221 (i.e., ejection start position P1) to the lower end portion of the second cover part 222, through-holes 212*a* are isolated from the particle storage space 217.

The particle supplying part 2*a* has a particle replenishment part 23*a* (in FIG. 12, the particle replenishment part 23*a* is shown by a chain double-dashed line, and the same applies to an after-mentioned level sensor 233) provided to the right end portion of the cylinder part 21*a* in FIG. 13. The particle replenishment part 23*a* is a screw feeder which has a screw therein, and replenishes particles into the particle storage space 217 of the cylinder part 21*a* from one end portion (the right end portion in FIG. 13) of the cylinder part 21*a* in the axial direction. A level sensor 233 is provided in the particle storage space 217. When the amount of particles stored in the particle storage space 217 becomes equal to or less than a certain level, replenishment of particles is performed. When particles are replenished into the particle storage space 217, air in the particle storage space 217 is exhausted mainly through the exhaust part 24. Even if particles go out into the exhaust part 24 from the cylinder part 21*a*, the particles are prevented by the filter 241 from going outside of the absorbent sheet manufacturing apparatus 1.

In the absorbent sheet manufacturing apparatus 1, the cylinder part 21*a* in FIG. 12 is rotated at a high speed around the rotation axis R1, so that particles in the particle storage space 217 are filled into through-holes 212*a* facing particles stored in the particle storage space 217 in the cylinder part 21*a*, out of the plurality of through-holes 212*a*. Until each through-hole 212*a* filled with particles reaches the ejection start position P1, the outer end of the through-hole 212*a* is closed (blocked) with the first cover part 221. The through-hole 212*a* is moved to a position opposed to the isolation part 25, and therefore the particles in the through-hole 212*a* is isolated (separated) from particles in the particle storage space 217. Then, when each through-hole 212*a* filled with particles passes the ejection start position P1 (i.e., the tip of the first cover part 221), the particles in the through-hole 212*a* are ejected toward the first sheet member 91.

Also in the absorbent sheet manufacturing apparatus 1 having the particle supplying part 2*a* in FIG. 12, the tangent line of the outer side surface 211 of the cylinder part 21*a* at the ejection start position P1 intersects with the outer side surface 311 of the first sheet conveying roller 31. In addition, the plurality of annular grooves 312 are formed on the outer side surface 311 of the first sheet conveying roller 31 at the same positions as those of the plurality of through-hole rows 213*a* of the cylinder part 21*a* with respect to the axial direction. Therefore, scattering of particles is reduced, and as a result, particles can be accurately fixed on the strip-like regions of the absorbent sheet 95 corresponding to the annular grooves 312.

Though the preferred embodiments of the present invention have been discussed above, the present invention is not limited to the above-discussed preferred embodiments, but allows various variations.

In the second sheet conveying roller 41, the plurality of annular grooves 412 corresponding to the plurality of concave portion rows 213 of the cylinder part 21 (or the plurality of through-hole rows 213*a* of the cylinder part 21*a*) are not necessarily formed, and for example, one annular groove having a width across the entire extent corresponding to all concave portion rows 213 with respect to the axial direction may be formed (the width of the annular groove is less than the width of the second sheet member 92). In this case, impact on particles which collide with the second sheet member 92 on the second sheet conveying roller 41 can be absorbed by a gap formed between the bottom surface of the annular groove and the second sheet member 92. If a groove extending along substantially the entire length of the outer side surface in the circumferential direction around the second central axis J2 is formed so as to face holes of the cylinder part, the groove isn't necessarily annular and the groove may be a spiral groove along the second central axis J2 on the outer side surface 411, for example.

Figure 14:
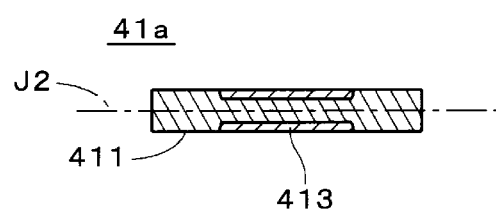
FIG. 14 is a view showing another example of second sheet conveying roller.

From the viewpoint of absorbing impact on particles which collide with the second sheet member 92 on the second sheet conveying roller 41, as shown in FIG. 14, a second sheet conveying roller 41*a* having an absorber (shock absorber) 413 on the outer side surface 411 which is a sponge, elastic rubber or the like configured to absorb impact on particles which collide with the second sheet member 92 thereon may be employed. The absorber 413 in FIG. 14 is annular around the second central axis J2 and is provided across the entire extent corresponding to all concave portion rows 213 of the cylinder part 21 with respect to the axial direction.

Depending on the design of the particle supplying part, for example, the first cover part 221 is omitted in the particle supplying part 2 of FIG. 1, and a suction mechanism for suctioning particles in each concave portion 212 of the cylinder part 21 to hold the particles therein may be provided additionally. In this case, the ejection start position is set as a position to release the suction in the suction mechanism.

In the absorbent sheet manufacturing apparatus 1, the annular grooves 412 of the second sheet conveying roller 41 (or absorber 413) can reduce scattering of particles on the second sheet conveying roller 41. Thus, even if not applying adhesive onto the first sheet member 91, particles can be fixed on the plurality of strip-like regions of the absorbent sheet with some accuracy. Depending on the design of the absorbent sheet, adhesive may be applied over the entire surface of the first sheet member 91.

In the bonding roller 51, there may be a case where an annular groove similar to that of the first sheet conveying roller 31 is formed, to avoid contact of both the first sheet conveying roller 31 and the bonding roller 51 with the strip-like regions (regions of the groove portions 911) on which particles are fixed in bonding between the first sheet member 91 and the second sheet member 92.

Depending on the design of the absorbent sheet manufacturing apparatus 1, there may be a case where the first sheet member 91 and the second sheet member 92 are bonded with each other between the second sheet conveying roller 41 and the first sheet conveying roller 31 and the bonding roller 51 is omitted. In this case, the second sheet conveying roller 41 realizes the sheet bonding part for bonding the second sheet member 92 on the first sheet member 91.

In the above preferred embodiment, discussion has been made on the manufacture (production) of the absorbent sheets 95 where the striped particle existence regions 951 are set, however, the technique where the annular grooves 412 (or absorber 413) of the second sheet conveying roller 41 reduce scattering of particles may be utilized for the manufacture of absorbent sheets 95 each having only one particle existence region 951.

In the above absorbent sheet manufacturing apparatus, particles of absorbent material are supplied such as crosslinked partially neutralized polyacrylic acid, hydrolyzed starch-acrylic acid graft polymer, saponified vinyl acetate-acrylic ester copolymer, hydrolyzed acrylonitrile copolymer, crosslinked acrylonitrile copolymer, hydrolyzed acrylamide copolymer, crosslinked acrylamide copolymer, crosslinked cationic monomers, or crosslinked polyamino acid.

Structure of the absorbent sheet manufacturing apparatus may be utilized for a sheet article manufacturing apparatus for manufacturing a deodorant sheet which is a sheet article for an absorbent article such as a disposable diaper or absorbent pad for light incontinence, by supplying particles of deodorant material such as activated carbon, silica, alumina, zeolite, ion-exchange resin, or molecular sieve onto the first sheet member 91.

The constituent elements of above-discussed preferred embodiments and modified examples may be appropriately combined with one another, as long as they are not mutually exclusive.

While the invention has been shown and described in detail, the foregoing description is in all aspects illustrative and not restrictive. It is therefore understood that numerous modifications and variations can be devised without departing from the scope of the invention.

REFERENCE SIGNS LIST

1 Absorbent sheet manufacturing apparatus
21, 21a Cylinder part
31 First sheet conveying roller
41, 41a Second sheet conveying roller
51 Bonding roller
61 First applying part
91 First sheet member
92 Second sheet member
95 Absorbent sheet
211, 311, 411 Outer side surface
212 Concave portion
212a Through-hole
412 Annular groove
413 Absorber
951 Particle existence region
J1, J2 Central axis
L1 Tangent line
P1 Ejection start position
R1 Rotation axis

The invention claimed is:

1. A sheet article manufacturing apparatus for manufacturing a sheet article for an absorbent article, comprising:
a cylinder part having an outer side surface which is generally cylindrical around a rotation axis along a horizontal direction, a plurality of holes each filled with particles of absorbent material or deodorant material being arranged on said outer side surface in a circumferential direction around said rotation axis, said outer side surface being rotated around said rotation axis in a predetermined rotation direction, said cylinder part ejecting said particles almost along a tangent line of said outer side surface at an ejection start position when each of said plurality of holes passes said ejection start position, said ejection start position being set in a vicinity of a lowermost portion in a cross section of said outer side surface which is orthogonal to said rotation axis;
a first sheet conveying roller which is located near said lowermost portion of said cylinder part, said first sheet conveying roller having an outer side surface which is generally cylindrical around a first central axis parallel to said rotation axis, said outer side surface being rotated around said first central axis in a rotation direction opposite to said rotation direction of said cylinder part to convey a first sheet member along said outer side surface which is a continuous sheet and cause said first sheet member to pass in the vicinity of said lowermost portion of said cylinder part;
a second sheet conveying roller which is located anterior to said lowermost portion of said cylinder part with respect to a moving direction of said outer side surface of said cylinder part at said lowermost portion, said second sheet conveying roller having an outer side surface which is generally cylindrical around a second central axis parallel to said rotation axis, for conveying a second sheet member along said outer side surface to the vicinity of said lowermost portion to place said second sheet member on said first sheet member which has been supplied with said particles, said second sheet conveying roller being positioned to provide an open space gap between said first sheet conveying roller and said second sheet conveying roller, said second sheet member being a continuous sheet; and
a sheet bonding part for bonding said second sheet member on said first sheet member;
wherein said second sheet conveying roller has an annular groove on said outer side surface, said annular groove extending along substantially the entire length of said outer side surface in a circumferential direction around said second central axis and facing holes of said cylinder part.

2. The sheet article manufacturing apparatus according to claim 1, wherein said plurality of holes are formed on said outer side surface of said cylinder part with respect to each of a plurality of positions in an axial direction parallel to said rotation axis, and said annular groove is formed on said outer side surface of said second sheet conveying roller with respect to each of said plurality of positions in said axial direction.

3. The sheet article manufacturing apparatus according to claim 2, further comprising an applying part for applying adhesive onto a plurality of strip-like regions lying on said first sheet member, said plurality of strip-like regions corresponding to said plurality of positions in said axial direction.

\* \* \* \* \*